(12) United States Patent
Munafo et al.

(10) Patent No.: US 10,223,515 B2
(45) Date of Patent: Mar. 5, 2019

(54) SLEEP DATA CHAIN OF CUSTODY

(71) Applicant: Sleep Data Services, LLC, San Diego, CA (US)

(72) Inventors: Dominic Munafo, San Diego, CA (US);
David French, La Jolla, CA (US);
Bretton Hevener, San Diego, CA (US);
William Hevener, San Diego, CA (US); Thinh Nguyen, San Diego, CA (US)

(73) Assignee: Sleep Data Services, LLC, San Diego, CA (US)

( * ) Notice: Subject to any disclaimer, the term of this patent is extended or adjusted under 35 U.S.C. 154(b) by 0 days.

(21) Appl. No.: 16/105,905

(22) Filed: Aug. 20, 2018

(65) Prior Publication Data

US 2019/0005220 A1    Jan. 3, 2019

Related U.S. Application Data

(63) Continuation of application No. 15/646,052, filed on Jul. 10, 2017, now Pat. No. 10,055,565, which is a
(Continued)

(51) Int. Cl.
*G06F 1/16* (2006.01)
*G06F 19/00* (2018.01)
(Continued)

(52) U.S. Cl.
CPC ............ *G06F 21/32* (2013.01); *G06F 1/163* (2013.01); *G06F 19/00* (2013.01); *G16H 10/60* (2018.01); *H04L 67/306* (2013.01)

(58) Field of Classification Search
CPC .......... G06F 21/32; G06F 19/00; G06F 21/83; G06F 2221/2139; G06F 3/017; G06F 19/3462; G06F 21/31; G06F 21/34
(Continued)

(56) References Cited

U.S. PATENT DOCUMENTS 5,233,987 A    8/1993  Fabian et al.
5,517,983 A    5/1996  Deighan et al.
(Continued)

FOREIGN PATENT DOCUMENTS

WO    WO-2001/071636 A2    9/2001
WO    WO-2003/043494 A1    5/2003
(Continued)

OTHER PUBLICATIONS

Google patents search, Jun. 19, 2017. 4 pages.
Google Patent Search History, Dec. 27, 2017. 2 pages.

*Primary Examiner* — Mark S Blouin
(74) *Attorney, Agent, or Firm* — Mintz Levin Cohn Ferris Glovsky and Popeo, P.C.

(57) ABSTRACT

A wearable device includes one or more biometric sensors, each of the one or more biometric sensors gathering biological data from a wearer of the wearable device, the wearable device further having a computer processor for receiving the biological data from the one or more biometric sensors and generating biometric information based on the biological data and according one or more biometrical algorithms, the biometric information including validation information to validate the wearer as a source of the biological data gathered by each of the one or more sensors, the biometric information further including sleep information to provide a sleep profile of the wearer.

12 Claims, 2 Drawing Sheets

Related U.S. Application Data continuation of application No. 15/481,362, filed on Apr. 6, 2017, now Pat. No. 9,760,703, which is a continuation of application No. 14/827,151, filed on Aug. 14, 2015, now Pat. No. 9,659,159.

(60) Provisional application No. 62/037,536, filed on Aug. 14, 2014.

(51) Int. Cl.
 *G06F 21/32* (2013.01)
 *G16H 10/60* (2018.01)
 *H04L 29/08* (2006.01)

(58) Field of Classification Search
 USPC .................................................. 340/5.82
 See application file for complete search history.

(56) References Cited

U.S. PATENT DOCUMENTS

| | | |
|---|---|---|
| 5,540,219 A | 7/1996 | Mechlenburg et al. |
| 5,715,812 A | 2/1998 | Deighan et al. |
| 5,765,563 A | 6/1998 | Vander Schaaf |
| 6,039,688 A | 3/2000 | Douglas et al. |
| 6,223,064 B1 | 4/2001 | Lynn et al. |
| 6,306,088 B1 | 10/2001 | Krausman et al. |
| 6,881,192 B1 | 4/2005 | Park |
| 7,413,549 B1 | 8/2008 | Koh |
| 7,942,824 B1 | 5/2011 | Kayyali et al. |
| 8,332,236 B2 | 12/2012 | Yurko et al. |
| 8,348,941 B2 | 1/2013 | Tehrani |
| 8,355,769 B2 | 1/2013 | Levendowski et al. |
| 8,655,717 B2 | 2/2014 | Schwarzberg et al. |
| 8,690,751 B2 | 4/2014 | Auphan |
| 8,744,803 B2 * | 6/2014 | Park ............... A61B 5/0002 702/160 |
| 8,903,671 B2 * | 12/2014 | Park ............... G08B 21/18 702/104 |
| 8,920,332 B2 * | 12/2014 | Hong .............. A61B 5/02427 600/500 |
| 9,148,483 B1 * | 9/2015 | Molettiere .......... H04L 67/22 |
| 9,159,223 B2 * | 10/2015 | Proud .............. H02J 7/025 |
| 9,227,032 B2 | 1/2016 | Kwok et al. |
| 9,283,399 B2 | 3/2016 | Donnelly et al. |
| 9,310,909 B2 * | 4/2016 | Myers ............... G06F 19/00 |
| 9,619,660 B1 | 4/2017 | Felix et al. |
| 9,760,703 B2 | 9/2017 | Munafo et al. |
| 2005/0119711 A1 | 6/2005 | Cho et al. |
| 2006/0218011 A1 | 9/2006 | Walker et al. |
| 2007/0032733 A1 | 2/2007 | Burton |
| 2007/0288266 A1 | 12/2007 | Sysko et al. |
| 2009/0265182 A1 | 10/2009 | Peterson et al. |
| 2009/0326981 A1 | 12/2009 | Karkanias et al. |
| 2011/0061647 A1 | 3/2011 | Stahmann et al. |
| 2012/0197353 A1 | 8/2012 | Donnelly et al. |
| 2013/0054215 A1 | 2/2013 | Stubna et al. |
| 2013/0216989 A1 | 8/2013 | Cuthbert |
| 2015/0169844 A1 | 6/2015 | Munafo et al. |
| 2016/0048671 A1 | 2/2016 | Munafo et al. |
| 2016/0199215 A1 | 7/2016 | Kopelman |
| 2016/0210440 A1 | 7/2016 | Munafo et al. |

FOREIGN PATENT DOCUMENTS

| | | |
|---|---|---|
| WO | WO-2005/066868 A2 | 7/2005 |
| WO | WO-2012/006524 A1 | 1/2012 |
| WO | WO-2015/074084 A1 | 5/2015 |
| WO | WO-2016/192941 A1 | 12/2016 |

\* cited by examiner

SLEEP DATA CHAIN OF CUSTODY

CROSS-REFERENCE TO RELATED APPLICATIONS

This application claims priority to and the benefit of U.S. Continuation application Ser. No. 15/481,362 filed on Apr. 6, 2017, titled "Sleep Data Chain of Custody", which claims priority to and the benefit of U.S. Non-Provisional application Ser. No. 14/827,151, no U.S. Pat. No. 9,659,159, filed on Aug. 14, 2015, titled, "Sleep Data Chain of Custody", which claims priority to and the benefit of U.S. Provisional Patent Application No. 62/037,536 filed on Aug. 14, 2014, titled, "Sleep Data Chain of Custody", which is hereby incorporated by reference in its entirety.

BACKGROUND

This document is related to sleep monitoring/tracking, and more particularly to a system and method for establishing manageable, verifiable and accurate chain of custody for sleep monitoring/tracking data.

Establishing such chain of custody for sleep regulation is crucial as mandated rest periods for employees become more common. Rest periods fall into three primary categories: those that are required by law; those that are not yet required by law but are garnering public support for implementation (for example, for physicians and other health care workers); and those that employers electively require to promote safer workplaces.

Thus far, increased monitoring/tracking of sleep has proven successful. For example, in the decade ending in 2011 in the trucking industry, large truck crashes declined 26 percent from 5,111 to 3,757, because new sleep research showed that working long hours daily and weekly eventually caused chronic fatigue, slow reaction times and reduced ability to assess situations, including personal fatigue levels. As another example, in 2010 and 2011, federal agencies tightened regulations governing rest periods for both airline pilots and air traffic controllers due to research supporting links between adequate rest and safety. Other transportation industries, including railroad and shipping groups, have voluntarily implemented better policies requiring adequate rest for workers. Some industry groups including the U.S. Occupational Safety and Health Administration, Accreditation Council for Graduate Medical Education, and the consumer-advocacy group Public Citizen, have been or will be considering whether better sleep and/or rest requirements for health care workers might ultimately benefit both professionals and patients.

Currently, there is no way to effectively monitor compliance with sleep requirements (i.e., whether employees are actually taking mandated rests.) This does not honor the spirit of the law, which is to promote safer environments for workers and the public. It also makes assessing the efficacy of these regulations difficult.

Some trucking companies have "electronic logs" situated near steering wheels, which record when the motor is on or off, whether or not the trucker is off-duty, and gas mileage. These devices prevent truckers from taking unauthorized short-cuts or driving over the speed limit, but they do not track whether drivers are sleeping. In some instances, they are also noisy and distracting.

Some professionals, for example, pilots and physicians, may be mandated or requested to self-report fatigue, sleepiness or exhaustion. However, they may feel professionally pressured to underreport these experiences. Additionally, exhausted individuals may not be able to recognize their own state of exhaustion.

What is needed is a more effective solution than self-reporting or electronic logs.

SUMMARY

This document presents a wearable sleep tracking device that maintains chain of custody of sleep-related, and biometric data, which can include time an individual is asleep and time the individual is awake or alert. The sleep tracking device can track a large number of data sources to maintain and ascertain various compliance thresholds with one or more configurable sleep-related regulations or requirements.

In one aspect, a wearable device includes one or more biometric sensors. Each of the one or more biometric sensors to gathering biological data from a wearer of the wearable device, the wearable device further having a computer processor for receiving the biological data from the one or more biometric sensors and generating biometric information based on the biological data and according one or more biometrical algorithms. The biometric information includes validation information to validate the wearer as a source of the biological data gathered by each of the one or more sensors. In some implementations, the biometric information includes sleep information to provide or generate a sleep profile of the wearer.

In some aspects, a system can further include a transceiver coupled with the wearable device, the transceiver for transmitting the biometric information as a digital signal to one or more web servers via a communications network. The system can further include a chain of custody engine associated with the wearable device, the chain of custody engine to provide a chain of custody validation for the biometric information from the wearer to the one or more web servers.

In other aspects, a computer-implemented method includes the steps of gathering, by one or more biological sensors of a wearable device, biological data from a wearer of the wearable device, and generating biometric information by a computer processor of the wearable device based on the biological data and according one or more biometrical algorithms. The biometric information includes validation information to validate the wearer as a source of the biological data gathered by each of the one or more sensors, the biometric information further including sleep information to provide a sleep profile of the wearer. The method further includes transmitting, by a transceiver coupled with the wearable device, the biometric information to one or more web servers via a communications network. The method further includes maintaining, by the computer processor, a chain of custody of the biometric information from the wearer to the one or more web servers.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

DETAILED DESCRIPTION

Figure 1:
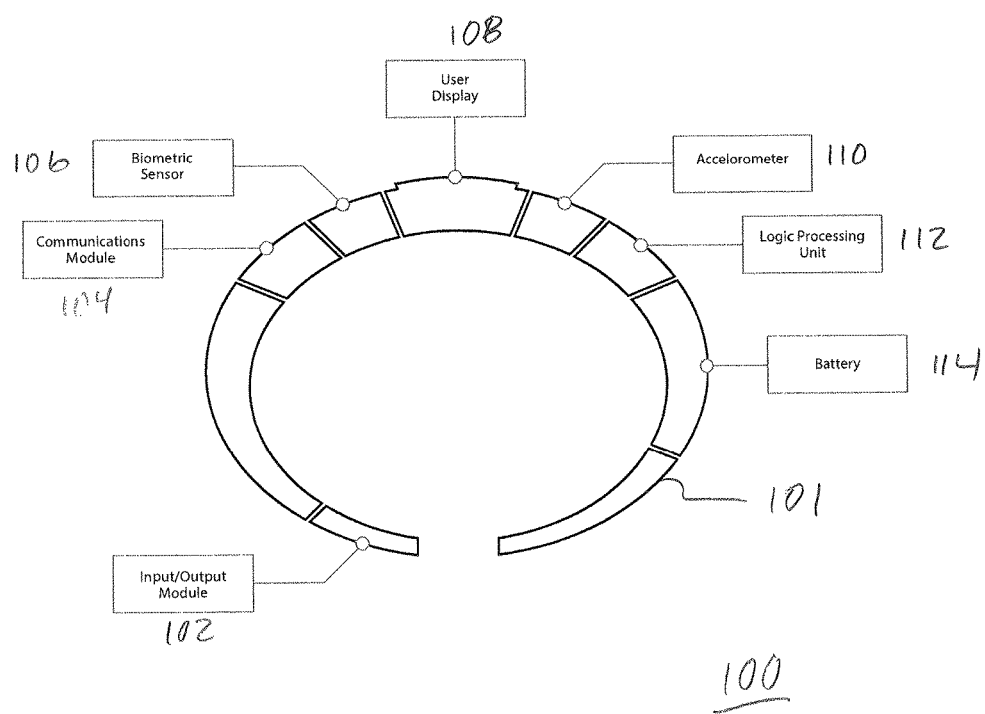
FIG. 1 illustrates a wearable sleep tracking device and its component parts.

This document describes a wearable sleep tracking device that gathers biometric information from a wearer, and that maintains chain of custody of sleep-related data generated from the biometric information.

The broad definition of chain of custody is considered as establishing the identity and integrity of physical evidence by tracing its continuous whereabouts. In the case of wearable sleep tracking devices, identity refers to the person whose rest was being monitored; for example, a truck driver, pilot, air traffic controller, or physician. Although the "evidence" collected and transmitted refers to physical quantities; for example, heart rate and other biometrics, here "integrity" refers to the direct and accurate relationship between the biometric data collected and the user. The chain of custody ascertains that the biometric data belongs to the user, throughout the data collection, transmission and aggregation processes. The data's "whereabouts" would be continuously monitored, user-tagged, assessed and stored in an impermeable loop between wearer and end-user.

The wearable sleep tracking device is configured to transfer data from the wearer to a centralized data aggregation and processing system. Examples of data might include actigraphy, GPS coordinates, time worn, and biometric data such as heart rate, EKG readings, skin temperature, and skin galvanic response. Thus, the wearable sleep tracking device can transmit data to a mobile phone or other intermediary device, which then transmits the data with or without processing via Internet pathways (wireless or otherwise) to a central server. In alternative implementations, the wearable sleep tracking device can include a transceiver for direct data transfer from the wearer to the central server. The central server traffics the data to a supervisor terminal or other consumption system.

In some implementations, the wearable sleep tracking device includes at least one sensor that is always in contact with the wearer, such as on the underside of a band, such that at random or programmed intervals the sensor takes a biometric reading to confirm that the authenticated user is wearing the device. This chain of custody confirmation can then be mapped by a computer with other data (GPS, timestamp, etc.) to determine if the wearer is in compliance. The ability to take a biometric reading without user interaction, such as requiring a wearer to touch a sensor, is important to validate chain of custody of the data collected and/or transferred by the wearable sleep tracking device while the wearer is asleep.

When the wearable sleep tracking device is unable to communicate to the central server, it will store any captured data locally for a period of time, until the next time it re-connects with the central server. Further, when the wearable sleep tracking device is not able to communicate directly to the centralized system, it communicates through a connected intermediary; i.e., a smartphone. This centralized system will analyze the data and provide data, information, and alerts to end-users. The chain of custody enables end-users to draw direct, accurate inferences regarding the wearer's episodic and/or accumulated rest patterns to ensure safety and legal compliancy. End-users include the wearer of the sleep tracking device, supervisors, regulatory agencies, etc.

In accordance with some preferred implementations, a device for maintaining chain of custody is a tamper-proof seal, akin to a lock snap. Physically this may employ the same technology as a plastic wristband: waterproof, lightweight, stretch-resistant, durable wristbands that lock into place with permanent locking snaps. The locking snap maintains chain of custody by assuring wearer connection with the sleep tracking device. If the wearer attempts to tamper with the device for removal or unauthorized transfer to another wearer (for example, a passenger in the vehicle) the tamper-proof seal would break.

For best compliance, the tamper-proof seal is preferably applied and monitored manually. This could introduce problems of inefficiency and manageability, requiring person-to-person examination of the tamper-proof seal for signs of damage. Given the physical effort that could be involved in some industries (for example, trucking) wearers with broken seals could make the plausible argument that the appearance of tampering, or a broken or missing lock, happened by accident. Applying, monitoring, repairing and replacing tamper-proof seals can be time-consuming and subject to human error.

While managed employees are subject to the company mandates and requirements provided by employers, independent contractors are not necessarily subject to these same requirements or may not be independently motivated to comply by applying tamper-proof seals. This creates issues of accountability, compared to managed employees. Tamper-proof seals interfere with functions related to recharging devices, or switching devices. (For example, an independently contracted trucker may ferry a container for one company on an outbound trip, but another company on the return trip. This makes tracking devices and users, and maintaining the chain of custody, a difficult task that becomes vulnerable to security breaches or data compromise.

Tamper-proof seals can be physically uncomfortable or distracting for drivers. Plastic wristbands and locking snaps are not designed for long-term use; most wearers limit use to hours or an evening; for example, a theme park or music concert. The cumbersome design could become irritating on long-distance trips because of shape, texture and other factors. Tamper-proof seals might potentially suggest a lack of trust between an employer and driver, resulting in the psychological factor of increased resentment at the notion of always being tracked. This could decrease wearer buy-in for the program, since the seal offers no compensatory benefits.

Accordingly, in some alternative implementations of a device for maintaining chain of custody, heartbeat and ECG information from a wearable device are used to authenticate that the data stream is coming from a specific user. Heartbeat authentication functions the way traditional fingerprinting functions: an individual's unique heartbeat pattern can provide positive identification. Heartbeats can securely communicate a wearer's identity to devices, including wearable devices. Cardiac rhythms function as smart passwords, wirelessly transmitting identity to wireless devices.

In some implementations, wearers place a finger on the device's top sensor, and allow their wrist to contact with the device's bottom sensor, completing an electrical circuit. The device alerts wearers than an electrical circuit has been completed by vibrating and illuminating LEDs. Wearers remain "authenticated" until the device is removed. In some cases, a "three factor security system" helps maintain the chain of custody. The system requires three factors present to complete the positive ID loop: a) the heartbeat tracking device b) the unique heartbeat and c) a third device, such as a smartphone, registered to the device application.

This concept combines heartbeat and ECG sensor and software with sleep tracking sensors and software available in existing consumer fitness and sleep trackers. The device's sensor and software maintains positive identification of the wearer, assuring that the wearer remains the same throughout data collection, transmission, and aggregation. The device can be removed for comfort, or during non-working hours. Further, the device can re-establish chain of custody through biometric authentication solely by the wearer.

Sleep tracking sensors and software monitor the wearer to determine periods of activity and rest. Data for body temperature, heart rate, movement and other factors can be assessed for indicators of adequate rest or sleep. If the sleep tracking and chain of custody data stream is tied to a GPS data stream (i.e., from a smartphone) then it can be inferred that the wearer of the device is at a specific location, within a margin of error (+/−30 feet) if the device is connected to the GPS via Bluetooth. The system can dynamically, in real time, respond to changes in location information and update or alert the supervisors as appropriate.

In some implementations, an exception can be made for when the wearer leaves the planned route/corridor can be preprogrammed into the system, or dynamically updated through human interaction. For example, alerts can be sent if the wearer leaves the preset route, or conversely, the tracking can be switched off if the wearer leaves the route.

This process can track mandated rest periods, and determine if the user is driving or not. In some implementations, an algorithm used by the wearable sleep tracking device is configured to determine between sustained driving versus in-town commuting. The system can switch off as needed or desired to accommodate truckers who are still wearing the device but no longer require the supervision or management of employers or regulatory agencies.

In accordance with the disclosure herein, a wearable sleep tracking device can maintain public safety by ensuring that regulated employees, such as truckers, pilots and air traffic controllers, receive the mandated rest periods required by federal agencies. The device and system can calculate metrics and values in a repeatable and automated matter to ascertain characteristics associated with sleep and rest.

FIG. 1 illustrates a wearable sleep tracking device 100, which is configured to be worn, attached to, or otherwise affixed to a part of a wearer's anatomy. The sleep tracking device 100 in FIG. 1 is shown as a bracelet or ankle cuff, but can be any type of attachable or wearable structure. The sleep tracking device 100 includes an input/output module 102 that can contain a transceiver or other I/O port, a communications module 104 that can format information collected by the sleep tracking device 100 in a format that can be transmitted by the input/output module 102, and one or more biometric sensors 106. The biometric sensors 106 can include, without limitation, a heartrate sensor, a breath rate sensor, a body temperature sensor, a blood pressure sensor, a sleep sensor, or other biometric sensor.

The sleep tracking device 100 further includes a user display 108 for displaying information collected by the one or more biometric sensors 106, or received by the sleep tracking device 100 via input/output module 102. For instance, the user display 108 can display feedback or instructions from a monitoring entity that monitors the wearer's sleep status remotely. The user display 108 can also display real-time data such as time, location, task or task status, or the like. The sleep tracking device 100 can further include an accelerometer 110 for monitoring acceleration and movement of the wearer of the sleep tracking device 100. The sleep tracking device 100 further includes a logic processing unit 112 for processing information collected by the sleep tracking device 100 via the one or more biometric sensors 106, or from the input/output module 102, or even the user display 108 (if the display also functions as a touch-sensitive input device). The sleep tracking device 100 may include a battery 114 or other power source. All of the above components of the sleep tracking device 100 can be housed in a housing 101, which can take any of a number of forms.

Figure 2:
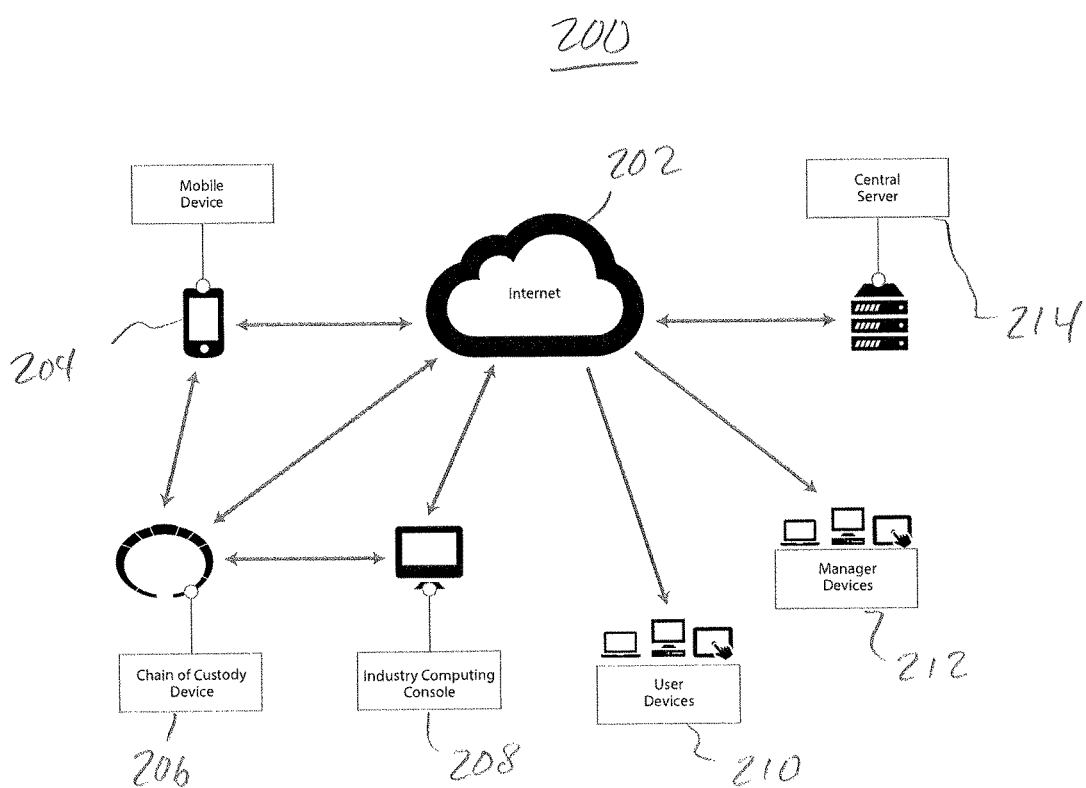
FIG. 2 is a block diagram of a wearable sleep tracking device and system.

FIG. 2 is a block diagram of a sleep tracking system 200. The system 200 includes one or more wearable devices 206, as substantially described above, which are in communication with a mobile device 204 and/or industry computing console 208. The industry computing console 208 can be programmed with logic to process and manage data to and from the wearable devices 206. The mobile device 204 can be associated with a wearer of the wearable device 206. In some implementations, communication can be executed through the internet 202, although other communication mediums can be utilized.

The system 200 further includes user devices 210, such as any number of computing devices used by the wearer or other employees or customers associated with the wearer, and manager devices 212. The manager devices 212 can include any number of computing devices that are pre-programmed with logic to assist a manager to monitor the activity of a wearer, such as described below. The system 200 further includes a central server 214 that can store some or all of the data accumulated or transmitted by the various computing devices or wearable devices of the system 200.

The systems and methods described herein can assure that the metrics and values represented by a device assigned to a particular wearer actually represent the wearer himself/herself rather than another party. These systems and methods provide this chain of custody in a manner that is manageable, feasible and cost-effective for employers, supervisors and regulatory agencies. Finally, the system and method provide this chain of custody in a manner that minimal disruption, discomfort, inconvenience, and intrusion for truckers and other wearers.

Wearers can self-monitor in order to independently and individually plan travel and rest times, assuring compliance with employer or legally mandated rest times. For instance, long-distance truckers have complained that adhering to rest regulations meant sometimes parking in unsafe areas for mandated rest. Planning ahead for primed sleep could help truckers locate safe, geographically optimized destinations for rest if wearable devices were synced with GPS data banks. In this context, supervisors can monitor data remotely from the wearable device to identify wearers who are intentionally or unintentionally not meeting required rest specifications. Supervisors could intervene as wearers approach non-compliance, by sending messages or alerts to the wearable device or other communication device, to remind wearers to plan for upcoming rests. Supervisors/logistics managers could also integrate sleep/rest intervals into route planning and other logistics systems.

Conversely, supervisors could monitor wearer wakefulness. For example, if heart rates, etc. were indicative of oncoming sleepiness in a truck driver or air traffic controllers, supervisors could intervene via alerts or other communication to prevent sleep onset. Regulatory agencies can monitor data depending on desired or legally required intervention levels. For example, companies with a record of non-compliance, or higher-risk industries, could be monitored more closely for non-compliance. Other external agencies, such as research institutions, might partner with employers for monitoring in order to research topics related to sleep, rest, safety, etc. and collect relevant data.

The system functionality could be integrated into logistics planning software so rest periods/downtime can be accommodated as part of the logistics planning, similar to how load weight and routing are factored into route planning. Because the wearable can provide real time, objective data on the activities of the wearer, this information can be used to customize any program to the specific behaviors of the wearer. For example, a cognitive behavior program can constantly change and adapt to address the issues that the wearer is experiencing at the time.

The systems and methods described herein offer practical, appealing incentive structures for worker compliance. For instance, in the trucking context, trucker compensation is often calculated based on a fee-mile-structure. To incentivize adoption and compliance for truckers, who may resist sleep or rest that interferes with their ability to quickly log miles, per-mile compensation can be increased. Although truckers completing required rest stops will necessarily be travelling more slowly, this slower pace will be offset by higher compensation rates for complying with mandated rest stops.

The systems and methods described herein also offer practical, appealing incentive structures for adopting companies. For example, motor vehicle crashes, including those that involve trucks, result in higher insurance premiums, wasted fuel (idling time, spilled fuel, etc.) and other costs (15). In some implementations, savings from lower premiums can be passed on as incentives for increasing the trucker mileage payments. Consumers (in this case, insured drivers) may be willing to trade increased transparency—via onboard diagnostic systems (OBDs) to track data such braking time, speed, etc.—for the possibility of lower insurance rates. Companies and drivers can log onto the system's real-time incentive tracking feature for estimates and real-time calculations on their projected discounts/incentives based on adopting the sleep-tracking wearable device chain of custody system.

Although a few embodiments have been described in detail above, other modifications are possible. Other embodiments may be within the scope of the following claims.

The invention claimed is:

1. An apparatus comprising:
    a wearable device having one or more biometric sensors and an authentication sensor, each of the one or more biometric sensors to gather biological data from a wearer of the wearable device, the authentication sensor providing authentication of the wearer of the wearable device, the wearable device further having a computer processor for receiving the biological data from the one or more biometric sensors and generating biometric information based on the biological data, the biometric information including validation information to validate the wearer as a source of the biological data gathered by each of the one or more sensors, the biometric information further including sleep information to provide a sleep profile of the wearer; and
    a chain of custody engine associated with the wearable device, the chain of custody engine to provide a chain of custody validation for the biometric information, validation information and the sleep information from the wearer to the one or more web servers to ensure compliance by the user of rules related to the gathering of the biological data.

2. The apparatus in accordance with claim 1, further comprising a transceiver coupled with the wearable device, the transceiver for transmitting the biometric information, validation information and sleep information as a digital signal to one or more web servers via a communications network.

3. The apparatus in accordance with claim 2, wherein the wearable device includes a housing to be worn around the wearer's wrist.

4. The apparatus in accordance with claim 3, wherein the authentication sensor is connected with the housing.

5. The apparatus in accordance with claim 1, wherein the wearable device further includes a positioning sensor to establish a geographical position of the wearer.

6. The apparatus in accordance with claim 1, wherein the wearable device further includes an accelerometer to determine a direction and rate of speed of the wearer.

7. The apparatus in accordance with claim 1, wherein the computer processor generates the biometric information according one or more biometrical algorithms.

8. A computer-implemented method for maintaining a chain of custody of data gathered from a wearer by one or more biological sensors of a wearable device, the method comprising:
    authenticating, by an authentication sensor connected with the wearable device, an identity of the wearer of the wearable device;
    generating biometric information by a computer processor of the wearable device based on the biological data and according one or more biometrical algorithms, the biometric information including validation information to validate the wearer as a source of the biological data gathered by each of the one or more sensors, the biometric information further including sleep information to provide a sleep profile of the wearer; and
    maintaining, by the computer processor, a chain of custody of the biometric information, validation information and the sleep information from the wearer to the one or more web servers to ensure compliance by the user of rules related to the gathering of the biological data and associated with the identity of the wearer.

9. The computer-implemented method in accordance with claim 8, further comprising:
    transmitting, by a transceiver coupled with the wearable device, at least one of the biometric information, the validation information and the sleep information to one or more web servers via a communications network.

10. The computer-implemented method in accordance with claim 8, further comprising:
    establishing, by a positioning sensor of the wearable device, a geographical position of the wearer.

11. The computer-implemented method in accordance with claim 8, further comprising:
    determining, by an accelerometer of the wearable device, a direction and rate of speed of the wearer.

12. The computer-implemented method in accordance with claim 8, wherein the authentication sensor is a heartbeat sensor to monitor cardiac rhythms of the wearer.

* * * * *